United States Patent [19]

Walsh

[11] Patent Number: 4,622,158
[45] Date of Patent: Nov. 11, 1986

[54] AQUEOUS SYSTEMS CONTAINING ORGANO-BORATE COMPOUNDS

[75] Inventor: Reed H. Walsh, Mentor, Ohio

[73] Assignee: The Lubrizol Corporation, Wickliffe, Ohio

[21] Appl. No.: 550,325

[22] Filed: Nov. 9, 1983

[51] Int. Cl.$^4$ ................. C10M 133/46; C10M 139/00
[52] U.S. Cl. .................................. 252/49.3; 252/49.5; 252/49.6
[58] Field of Search ............... 252/49.3, 49.6, 49.5

[56] References Cited

U.S. PATENT DOCUMENTS

| | | | |
|---|---|---|---|
| 2,214,152 | 9/1940 | Wilkes | 252/49.5 X |
| 2,581,132 | 1/1952 | Nelson et al. | 252/49.5 X |
| 2,733,210 | 1/1956 | Taylor, Jr. | 252/49.3 |
| 2,811,489 | 10/1957 | Laug | 252/49.5 X |
| 3,169,923 | 2/1965 | Guarnaccio et al. | 252/32.5 |
| 3,186,946 | 6/1965 | Sluhan | 252/49.3 X |
| 3,195,332 | 7/1965 | Ranauto | 252/49.3 X |
| 3,429,909 | 2/1969 | Schuster | 252/49.3 X |
| 3,505,226 | 4/1970 | Cyba | 252/49.6 |
| 3,574,100 | 4/1971 | Wetmore | 252/49.3 X |
| 4,257,902 | 3/1981 | Singer | 252/18 |
| 4,298,486 | 11/1981 | Horodysky et al. | 252/49.6 |
| 4,382,006 | 5/1983 | Horodysky | 252/49.6 |
| 4,400,284 | 8/1983 | Jessup et al. | 252/49.6 |
| 4,406,802 | 9/1983 | Horodysky et al. | 252/49.6 |
| 4,410,436 | 10/1983 | Holstedt et al. | 252/46.4 |

OTHER PUBLICATIONS

Hackh's Chemical Dictionary, 3rd edition, McGraw-Hill Book Company, p. 138.

*Primary Examiner*—Jacqueline V. Howard
*Attorney, Agent, or Firm*—Joseph P. Fischer; Denis A. Polyn; James L. Cordek

[57] ABSTRACT

A composition is disclosed which comprises an aqueous phase and dispersed or dissolved in said aqueous phase an organo-borate compound having the formula

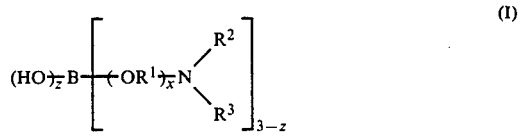

or

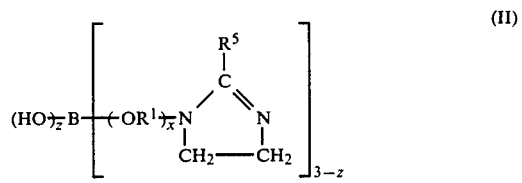

wherein
$R^1$ is a divalent hydrocarbon-based group,
$R^2$ is a hydrocarbon-based group or a group of the formula $-(R^4O)_yH$,
$R^3$ and $R^5$ are hydrocarbon-based groups,
$R^4$ is a divalent hydrocarbon-based group,
x is an integer of at least 1,
y is an integer of at least 1,
the sum of x and y has an average in the range of about 2 to about 75, and
z is 0, 1 or 2.

Aqueous concentrates and water-based functional fluids containing the above compositions are also disclosed.

30 Claims, No Drawings

AQUEOUS SYSTEMS CONTAINING ORGANO-BORATE COMPOUNDS

TECHNICAL FIELD

This invention relates to aqueous systems containing organo-borate compounds. More particularly, this invention relates to compositions containing an aqueous phase and an organo-borate compound dispersed or dissolved in such aqueous phase. Specifically, this invention relates to water-based functional fluids containing an organo-borate compound. The organo-borate compound is useful in imparting thickening and/or anti-wearing characteristics to such functional fluids. This invention also relates to aqueous concentrates containing such organo-borate compounds.

BACKGROUND OF THE INVENTION

The term "water-based functional fluid" is used herein to refer to water-based lubricants, hydraulic fluids, cutting fluids and the like. The use of water-based functional fluids is not a new concept. However, in recent times, the increasing cost and scarcity of petroleum has made it increasingly desirable to replace oil-based fluids with water-based fluids wherever possible. Other benefits can also flow from such replacements such as decreased fire hazard and environmental pollution problems. In many cases, however, it is not feasible to make such replacements because the water-based fluids cannot be modified in their properties so as to perform to the same high degree as their oil-based counterparts. For example, it has been often difficult, if not impossible, to replace certain oil-based hydraulic fluids with water-based fluids even though the desirability of doing so is evident.

A considerable amount of interest has been expressed in thickening water-based functional fluids to overcome performance limitations associated with unthickened fluids. These limitations involve, for example, the following general functions: improved fine feed control of valving for precise clamping and positioning operations; and improved pump efficiency by reducing internal leakage (particularly in vane pumps).

Various thickening agents for use in water-based functional fluids have been proposed. Examples of these thickening agents include the polysaccharides and various synthetic thickening polymers. Among the polysaccharides are the natural gums such as gum agar, gum Arabic, dextran, cellulose ethers and esters such as hydroxyethyl cellulose and the sodium salt of carboxymethyl cellulose. Other thickeners include synthetic polymers such as polyacrylates, polyacrylamides, hydrolyzed vinyl esters, polyvinyl pyrrolidones and homo- or copolymers as well as soluble salts of styrene, maleic anhydride copolymers. See, for example U.S. Pat. Nos. 2,455,961; 2,944,976; 2,956,951; 3,005,776; and 4,257,902.

The use of water-based functional fluids containing anti-wear agents is also not new. Examples of such anti-wear agents include dibutyl ammonium laurate. See, for example, U.S. Pat. Nos. 2,944,976 and 4,257,902.

There is a continuing need for organic thickening agents that are suitable for use in water-based functional fluids. It would be advantageous if such a thickening agent could be provided that also imparted other advantageous properties, such as anti-wearing characteristics, to such functional fluids.

SUMMARY OF THE INVENTION

The present invention contemplates the provision of an organic thickening agent that is suitable for use in water-based functional fluids. This agent provides the additional advantage of imparting, under various advantageous circumstances, anti-wearing characteristics to such fluids. Broadly stated, the present invention provides for a composition comprising an aqueous phase and dispersed in said aqueous phase an organo-borate compound having the formula

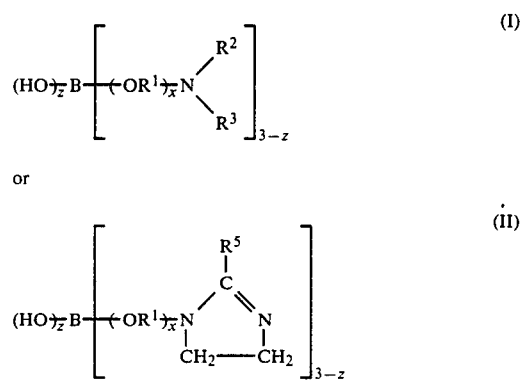

wherein $R^1$ is a divalent hydrocarbon-based group, $R^2$ is a hydrocarbon-based group or a group of the formula $-(R^4O)_yH$, $R^3$ and $R^5$ are hydrocarbon-based groups, $R^4$ is a divalent hydrocarbon-based group, x is an integer of at least 1, y is an integer of at least 1, the sum of x and y has an average in the range of about 2 to about 75, and z is 0, 1 or 2.

DESCRIPTION OF THE PREFERRED EMBODIMENTS

The compositions of the present invention include an aqueous phase, which is preferably the continuous phase of such compositions, and at least one organo-borate compound of Formula (I) or (II) dispersed or dissolved in such aqueous phase. $R^1$ preferably has an average of 1 to about 8 carbon atoms and more preferably is ethylene or propylene. $R^2$ can be a hydrocarbon-based group which preferably has an average of 1 to about 100 carbon atoms, more preferably about 8 to about 25 carbon atoms. Alternatively and preferably, $R^2$ is an alkoxy group having the formula

wherein $R^4$ is a divalent hydrocarbon-based group which preferably contains an average of from 1 to about 8 carbon atoms and more preferably is ethylene or propylene, and y is an integer ranging from 1 to about 50, preferably from 1 to about 25, more preferably from 1 to about 9, and advantageously from 1 to about 5. $R^3$ and $R^5$ are each hydrocarbon-based groups which preferably have an average of from 1 to about 100 carbon atoms, more preferably from about 8 to about 25 carbon atoms and advantageously from about 10 to about 20 carbon atoms. x is an integer ranging from 1 to about 50, preferably from 1 to about 25, more preferably from 1 to about 9, and advantageously from 1 to about 5. The sum of x and y ranges from 2 to about 75, preferably from about 2 to about 50, more preferably from about 2 to about 15, and advantageously from about 5 to about 10. z is 0, 1 or 2, and preferably is 0.

As used herein, the term "hydrocarbon-based group" denotes a group having a carbon atom directly attached to the remainder of the molecule and having a predominantly hydrocarbon character within the context of this invention. Such groups include the following:

(1) Hydrocarbon groups; that is, aliphatic, (e.g., alkyl or alkenyl), alicyclic (e.g., cycloalkyl or cycloalkenyl), aromatic, aliphatic-, and alicyclic-substituted aromatic, aromatic-substituted aliphatic and alicyclic groups, and the like, as well as cyclic groups wherein the ring is completed through another portion of the molecule (that is, two indicated hydrocarbon groups, e.g., $R^2$ and $R^3$, may together form an alicyclic group and such group may contain heteroatoms such as nitrogen, oxygen or sulfur). Such groups are known to those skilled in the art; representative examples include methyl, ethyl, butyl, hexyl, octyl, decyl, dodecyl, tetradecyl, octadecyl, eicosyl, cyclohexyl, phenyl and naphthyl and the like including all isomeric forms of such groups and when two hydrocarbon groups together form an alicyclic group, then examples of such groups include morpholinyl, piperidyl, piperazinyl, phenothiazinyl, pyrrolyl, pyrrolidyl, thiazolidinyl and the like.

(2) Substituted hydrocarbon groups; that is, groups containing non-hydrocarbon substituents which, in the context of this invention, do not alter the predominantly hydrocarbon character of the group. Those skilled in the art will be aware of suitable substituents; representative examples are hydroxy (HO—); alkoxy (RO—);

carbalkoxy (ROC(=O)—); acyl (RC(=O)—); acyloxy (RCO(=O)—);

carboxamide ($H_2NC(=O)$—); acylimidazyl (RC(=NR)—);

nitro (—$NO_2$); and alkylthio (RS—) and halogen (e.g., F, Cl, Br and I).

(3) Hetero groups; that is groups which, while predominantly hydrocarbon in character within the context of this invention, contain atoms other than carbon present in a chain or ring otherwise composed of carbon atoms. Suitable hetero atoms will be apparent to those skilled in the art and include, for example, nitrogen, oxygen and sulfur.

In general, no more than about three substituents or hetero atoms, and preferably no more than one, will be present for each 10 carbon atoms in the hydrocarbon-based group.

The organo-borate compounds of the present invention are prepared by the reaction of a boron compound selected from the group consisting of boric acid, boron trioxide or boric acid esters of the formula $B(OR)_3$ wherein R is a hydrocarbon-based group containing an average of from 1 to about 8 carbon atoms, preferably from 1 to about 4 carbon atoms, with the appropriate amine selected from the formulae:

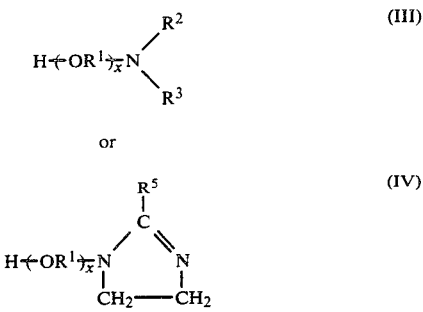

The amines represented by Formula (III) are used in preparing the organo-borate compounds represented by Formula (I). Similarly, the amines represented by Formula (IV) are used in preparing the organo-borate compounds represented by Formula (II). $R^1$, $R^2$, $R^3$, $R^4$, $R^5$, x and y in Formulae (III) and (IV) have the same meaning as in Formulae (I) and (II).

Representative examples of the amines of Formulae (III) or (IV) include monoalkoxylated amines such as dimethylethanolamine, diethylethanolamine, dibutylethanolamine, diisopropylethanolamine, di(2-ethylhexyl)ethanolamine, phenylethylethanolamine, dibutylisopropanolamine, dimethylisopropanolamine and the like and polyalkoxylated amines such as methyldiethanolamine, ethyldiethanolamine, phenyldiethanolamine, diethyleneglycol mono-N-morpholinoethyl ether, N-(2-hydroxyethyl)thiazolidine, 3-morpholinopropyl(2-hydroxyethyl)cocoamine, N-(2-hydroxy-ethyl)-N-tallow-3-aminomethylpropionate, N-(2-hydroxyethyl)-N-tallow acetamide, 2-oleoylethyl(2-hydroxyethyl)tallowamine, N'-[2-hydroxyethylaminoethyl]thiazole, 2-methoxyethyl(2-hydroxyethyl)tallowamine, N-[2-hydroxyethylaminoethyl]imidazole, N-[N'-octadecenyl-N'-2-hydroxy ethyl-aminothyl]phenothiazine, 2-hydroxydicocamine, 2-heptadecenyl-1-(2-hydroxyethyl)-imidazoline, 2-dodecyl-1-(5-hydroxypentyl)imidazoline, 2-(3-cyclohexylpropyl)-1-(2-hydroxyethyl)imidazoline and the like.

In a particularly advantageous embodiment of the present invention, the amines represented by Formula (III) are tertiary amines having one fatty alkyl group (derived from various fatty sources having from about 12 to about 18 carbon atoms) and two polyoxyethylene groups attached to the nitrogen atom. These tertiary amines can be represented by the following formula:

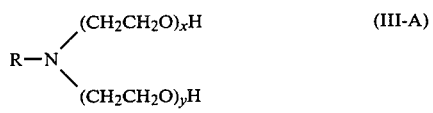

wherein R is the above-identified alkyl group of about 12 to about 18 carbon atoms, x and y are integers of at least one, and the sum of x and y ranges from 2 to about 50, preferably from about 2 to about 15, and advantageously from about 5 to about 10. A particularly preferred group of these amines are the "Ethomeens", a series of commercial mixtures of ethoxylated fatty amines available from Armak Company. Suitable "Ethomeens" include "Ethomeen S/15" (the alkyl group being derived from soya fatty acid and the sum of x and y being 5), "Ethomeen S/20" (the source of the alkyl group being soya fatty acid and the sum of x and y being 10), "Ethomeen T/15" (the source of the alkyl group being tallow fatty acid and the sum of x and y being 5), "Ethomeen T/12" (the source of the alkyl group being tallow fatty acid and the sum of x and y being 2), "Ethomeen O/12" (the source of the alkyl group being oleic acid and the sum of x and y being 2), "Ethomeen C/12" (the source of the alkyl group being coco fatty acid and the sum of x and y being 2), "Ethomeen C/15" (the source of the alkyl group being coco fatty acid and the sum of x and y being 5), "Ethomeen S/25" (the source of the alkyl group being soya fatty acid and the sum of x and y being 15), "Ethomeen C/20" (the source of the alkyl group being coco fatty acid and the sum of x and y being 10), "Ethomeen S/12" (the source of the alkyl group being soya fatty acid and the sum of x and y being 2), "Ethomeen 18/12" (the source of the alkyl group being stearic acid and the sum of x and y being 2), "Ethomeen 18/25" (the source of the alkyl group being stearic acid and the sum of x and y being 15). Preferred Ethomeens include Ethomeen S/15, Ethomeen S/20, and Ethomeen T/15.

In another preferred embodiment of the present invention, the amines represented by Formula (III) are the reaction products of a diamine and ethylene oxide and are represented by the formula:

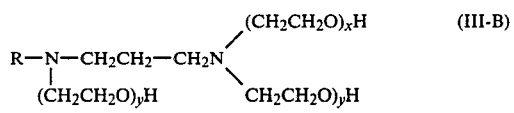
(III-B)

These amines are obtained from N-alkyltrimethylenediamines. R is an alkyl group of about 12 to about 18 carbon atoms. A particularly preferred group of these amines are the "Ethoduomeens", which are also a series of commercial mixtures of ethoxylated fatty amines available from Armak Company. Suitable "Ethoduomeens" include "Ethoduomeen T/13" (the source of the alkyl group being tallow fatty acid and the sum of x and y being 3), and "Ethoduomeen T/25" (the source of the alkyl group being tallow fatty acid and the sum of x and y being 15).

The organo-borate compounds of the present invention can be prepared by adding the boron reactant (e.g., boric acid) to at least one of the amine reactants represented by Formulae (III) or (IV) in a suitable reaction vessel, and heating the resulting reaction mixture to a temperature ranging from about 50° C. to about 300° C., preferably from about 100° C. to about 250° C., more preferably about 150°–230° C., with continuous stirring. The reaction is continued until by-product water ceases to evolve from the reaction mixture indicating completion of the reaction. The removal of by-product water is facilitated by either blowing an inert gas, such as nitrogen, over the surface of the reaction mixture or by conducting the reaction at reduced pressures.

Although normally the amine reactants are liquid at room temperature, in those instances where the amine reactant is a solid or semi-solid it is preferable to heat the amine to above its melting point in order to liquify it prior to the addition of the boron-containing reactant.

The amine reactant can serve as the solvent for the reaction mixture of the boron containing reactant and amine reactant. However, if desired, an inert normally liquid organic solvent such as mineral oil, naptha, benzene, toluene or xylene can be used as the reaction media. It is preferred to conduct the reaction using the amine reactant as the sole solvent.

If desired, the amine reactants represented by Formulae (III) or (IV) can be reacted first with elemental sulfur to sulfurize any carbon-to-carbon double bond unsaturation which may be present in the hydrocarbon-based groups $R^2$, $R^3$ or $R^5$ when these radicals are, for example, alkenyl radicals (e.g., fatty oil or fatty acid groups). The sulfurization reaction is carried out at temperatures ranging from about 100° C. to about 250° C., preferably from about 150° C. to about 200° C. The molar ratio of sulfur to amine ranges from about 0.5:1 to about 3:1, preferably 1:1. Generally no catalyst is required to promote sulfurization of any carbon-to-carbon double bond unsaturation which may be present in any amine reactants of this invention. However, catalysts may be employed. These catalysts are preferably tertiary hydrocarbon-substituted amines such as trialkylamines. Representative examples of these catalysts include tributylamine, dimethyloctylamine, triethylamine and the like.

Examples 1–17 are illustrative of the preparation of organo-borate compounds within the scope of the present invention. Unless otherwise indicated, all parts and percentages disclosed in these examples as well as throughout the specification and in the appended claims are by weight.

EXAMPLE 1

A mixture of 3247 parts of Ethomeen S/15 and 166 parts boric acid are heated with stirring and nitrogen blowing to 100° C. to dissolve the boric acid. The temperature is increased to 180° C. for 3–4 hours while water is removed. The mixture is filtered with a filter aid and the product, which is the filtrate, is a clear fluid.

EXAMPLE 2

A mixture of 2658 parts of Ethomeen T/15 and 124 parts of boric acid are heated with stirring and nitrogen-blowing (at a rate of two standard cubic feet per hour) until water begins to evolve. The temperature of the mixture is raised to 190° C. and maintained at that level for 3–4 hours while water is removed. The mixture is filtered through a filter aid and the filtrate, which is the product, is a light-brown fluid.

EXAMPLE 3

A mixture of 2115 parts Ethomeen S/20 and 62 parts boric acid are heated with stirring and nitrogen blowing (at a rate of two standard cubic feet per hour) to 100° C. Water begins to condense and is removed. The temperature of the mixture is raised to 180° C. while water is removed over a 3.5 hour period. The reaction is complete when water ceases to be evolved. The mixture is filtered through a filter aid. The filtrate, which is the product, is a clear fluid.

EXAMPLE 4

A mixture of 702 parts (6 moles) of 2-diethylaminoethanol, 124 parts (2 moles) of boric acid and 500 parts of toluene is heated to boiling under nitrogen, with stirring, and water is removed by azeotropic distillation. When water removal is complete, the mixture is vacuum stripped and filtered. The filtrate is the desired boron-containing product.

EXAMPLE 5

A mixture of 2100 parts (6 moles) of Ethomeen T/12 and 124 parts (2 moles) of boric acid is blown with nitrogen at 100°–220° C., with stirring, as water is removed by distillation. The mixture is cooled to 140° C. and filtered, using a filter aid material. The filtrate is the desired boron-containing product.

EXAMPLE 6

A mixture of 2100 parts (6 moles) of Ethomeen T/12 and 124 parts (2 moles) of boric acid is heated to 100° C. with stirring. The reaction vessel is then gradually evacuated as water is removed by distillation over 2.5 hours. The final temperature and pressure are 170° C. and 15 torr, respectively. The mixture is filtered, using a filter aid material. The filtrate is the desired boron-containing product.

EXAMPLE 7

A mixture of 1053 parts (3 moles) of Ethomeen O/12 and 62 parts (1 mole) of boric acid is blown with nitrogen and heated to 180° C. with stirring. Water is removed by distillation. The mixture is filtered through a filter aid material. The filtrate is the desired boron-containing product.

EXAMPLE 8

A boron-containing product is prepared from 2138 parts (7.5 moles) of Ethomeen C/12 and 155 parts (2.5 moles) of boric acid using the procedure described in Example 5.

EXAMPLE 9

A boron-containing product is prepared from 1269 parts (3 moles) of Ethomeen C/15 and 62 parts (1 mole) of boric acid, using the procedure described in Example 5 with the exception that the maximum reaction temperature is about 130° C.

EXAMPLE 10

A boron-containing product is prepared from 1476 parts (3 moles) of Ethomeen S/15 and 62 parts (1 mole) of boric acid, using the procedure described in Example 5 with the exception that the maximum reaction temperature is 160° C.

EXAMPLE 11

A boron-containing product is prepared from 1057.5 parts (1.5 moles) of Ethomeen S/20 and 31 parts (0.5 mole) of boric acid, using the procedure described in Example 5 with the exception that the maximum reaction temperature is 160° C.

EXAMPLE 12

A boron-containing product is prepared from 1392 parts (1.5 moles) of Ethomeen S/25 and 31 parts (0.5 mole) of boric acid using the procedure described in Example 5.

EXAMPLE 13

A mixture of 2430 parts (9 moles) of Ethoduomeen T/13, 186 parts (3 moles) of boric acid and 400 parts of xylene is heated under reflux, with nitrogen blowing, as water is removed by distillation. When water removal is complete, the mixture is vacuum stripped to remove volatiles. The mixture is diluted with mineral oil and filtered. The filtrate is an oil solution of the desired boron-containing product.

EXAMPLE 14

A mixture of 2100 parts (6 moles) of Ethomeen T/12 and 124 parts (2 moles) of boric acid, is blown with nitrogen at 100°–230° C., with stirring, while the water formed is removed. After cooling, 550 parts (2 moles) of oleic acid is added and the mixture heated to 240° C. with stirring and nitrogen blowing to remove water. The mixture is cooled and filtered. The filtrate is the desired boron-containing product.

EXAMPLE 15

A mixture of 62 parts (1 mole) of boric acid and 1152 parts (3 moles) of the alcohol which is derived from the reaction of equal molar amounts of $C_{16}$ alpha-olefin epoxide and aminopropylmorpholine is heated to 210° C. while removing the water of condensation. The mixture is filtered using filter aid to give the desired boron-containing product.

EXAMPLE 16

A boron-containing product is prepared by heating a mixture of 1050 parts (3 moles) of 1-hydroxyethyl-2-heptadecenyl imidazoline with 62 parts (1 mole) of boric acid to 180° C. while removing the water formed. The mixture is then filtered. The filtrate is the desired product.

EXAMPLE 17

A mixture of 2106 parts (3 moles) of Ethomeen T/12, 96 parts (3 moles) of sulfur and 0.03 mole tributylamine catalyst is heated to 180° C. for several hours. The resulting sulfurized product is cooled and 62 parts (1 mole) of boric acid is added. The mixture is heated to 200° C. and the water formed is removed by nitrogen blowing. The mixture is filtered through filter aid to give the desired boron, nitrogen and sulfur-containing product.

The compositions of the present invention contain a sufficient amount of water to disperse or dissolve the organo-borate compound. These compositions are characterized by an aqueous phase and, preferably, the level of water is sufficient so that the aqueous phase is the continuous phase of such compositions. The level of water required to disperse or dissolve the organo-borate is dependent on the dispersability or solubility of such borates, the determination of such dispersabilities or solubilities being within the skill of the art. These compositions can be prepared by adding the organo-borate to water (or by adding water to the organo-borate) using standard mixing techniques within the skill of the art.

The organo-borate compounds of the present invention function primarily as thickeners. Thus, when such compounds are employed as thickeners in water-based functional fluids, the level of addition will generally be a "thickening amount", that is, an effective amount to provide the functional fluid to which such compounds are dispersed or dissolved with the desired amount of thickening or increase in viscosity. The amount of organo-borate required to provide such a desired thickening or increase in viscosity is dependent on the particular organo-borate used and the functional fluid to which it is added, the determination of such amounts being within the skill of the art.

The organo-borate compounds of the invention also under various advantageous circumstances impart anti-wear characteristics to the functional fluids to which they are added. Thus, when such compounds are employed as anti-wear agents, the level of addition will generally be an "anti-wearing amount", that is, an effective amount to provide the functional fluid to which such compounds are dispersed or dissolved with the desired anti-wearing characteristics. The amount of organo-borate required to provide such anti-wearing properties is dependent on the particular organo-borate compound used and the functional fluid to which the compound is added, the determination of such amounts being within the skill of the art.

The terms "dispersed" and "dissolved" are used throughout this specification and in the appended claims to refer to the distribution of the organo-borate compounds of the invention in the aqueous phase to which they are added. While the practice of the present invention is not dependent on any particular theory or hypothesis to explain the invention, it should be understood that in some instances, the organo-borate compounds dissolve in the aqueous phase to form true solutions while in other instances, micelle dispersions or microemulsions are formed which visibly appear to be true solutions. Whether a solution, micelle dispersion, or microemulsion is formed, is dependent on the particular organo-borate compound employed and the particular system to which it is added. In any event, the terms "dispersed" and "dissolved" are used interchangeably throughout this specification and in the appended claims to refer to solutions, micelle dispersions, microemulsions and the like.

The invention includes aqueous systems containing at least about 25% water. Such aqueous systems encompass both concentrates containing about 25% to about 70%, preferably about 40% to about 70%, and advantageously about 40% to about 65% water; and water-based functional fluids containing from about 0.1 to about 15%, preferably about 0.1 to about 10%, and advantageously about 0.1 to about 5% by weight of the organo-borate compounds of the invention. The concentrates generally contain less than about 50%, generally less than about 25%, preferably less than about 15%, and more preferably less than about 6% hydrocarbyl oil. The water-based functional fluids contain less than about 15%, preferably less than about 5%, and more preferably less than about 2% hydrocarbyl oil. These concentrates and water-based functional fluids can optionally include other conventional additives commonly employed in water-based functional fluids. These other additives include dispersant/solubilizers, surfactants, functional additives, corrosion-inhibitors, shear stabilizing agents, bactericides, dyes, water-softeners, odor masking agents, anti-foam agents, and the like.

The concentrates are analogous to the water-based functional fluids except that they contain less water (i.e., less than about 70%) and proportionately more of the other ingredients. The concentrates can be converted to water-based functional fluids by dilution with water. This dilution is usually done by standard mixing techniques. This is often a convenient procedure since the concentrate can be shipped to the point of use before additional water is added. Thus, the cost of shipping a substantial amount of the water in the final water-based functional fluid is saved. Only the water necessary to formulate the concentrate (which is determined primarily by ease of handling and convenience factors), need be shipped.

Generally these water-based functional fluids are made by diluting the concentrates with water, wherein the ratio of water to concentrate is in the range of about 80:20 to about 99:1 by weight. As can be seen when dilution is carried out within these ranges, the final water-based functional fluid contains, at most, an insignificant amount of hydrocarbyl oil. This clearly distinguishes them from soluble oils.

Also included within the invention are methods for preparing aqueous systems, including both concentrates and water-based functional fluids, containing other conventional additives commonly employed in water-based functional fluids. These methods comprise the steps of:

(1) mixing the organo-borate compound of the invention with such other conventional additives either simultaneously or sequentially to form a dispersion/solution; optionally (2) combining said dispersion/solution with water to form said aqueous concentrates; and/or (3) diluting said dispersion/solution or concentrate with water wherein the total amount of water used is in the amount required to provide the desired concentration of organo-borate compound and other functional additives in said concentrates or said water-based functional fluids. These mixing steps are carried out using conventional equipment and generally at room or slightly elevated temperatures, usually below 100° C. and often below 50° C. As noted above, the concentrate can be formed and then shipped to the point of use where it is diluted with water to form the desired water-based functional fluid. In other instances the finished water-based functional fluid can be formed directly in the same equipment used to form the concentrate or dispersion/solution.

The dispersant/solubilizers that are useful in accordance with the present invention include the nitrogen-containing, phosphorus-free carboxylic solubilizers disclosed in U.S. Pat. Nos. 4,329,249 and 4,368,133. These patents are incorporated herein by reference. Briefly, these dispersant/solubilizers are made by reacting (I) at least one carboxylic acid acylating agent having at least one hydrocarbyl-based substituent of at least about 12 to about 500 carbon atoms with (II) at least one (a) N-(hydroxyl-substituted hydrocarbyl) amine, (b) hydroxyl-substituted poly(hydrocarbyloxy) analog of said amine or (c) mixtures of (a) and (b). Preferred acylating agents include the substituted succinic acids or anhydrides. Preferred amines include the primary, secondary and tertiary alkanol amines or mixtures thereof. These dispersant/solubilizers are preferably used at effective levels to disperse or dissolve the various other additives, particularly the functional additives discussed below, in the concentrates and/or water-based functional fluids of the present invention. In a particularly preferred embodiment of the present invention, the dispersant/solubilizer is the reaction product of a polyisobutenyl-substituted succinic anhydride with a mixture of diethylethanolamine and ethanolamine.

The surfactants that are useful can be of the cationic, anionic, nonionic or amphoteric type. Many such surfactants of each type are known to the art. See, for example, McCutcheon's "Emulsifiers & Detergents", 1981, North American Edition, published by McCutcheon Division, MC Publishing Co., Glen Rock, N.J.

U.S.A., which is hereby incorporated by reference for its disclosures in this regard.

Among the nonionic surfactant types are the alkylene oxide-treated products, such as ethylene oxide-treated phenols, alcohols, esters, amines and amides. Ethylene oxide/propylene oxide block copolymers are also useful nonionic surfactants. Glycerol esters and sugar esters are also known to be nonionic surfactants. A typical nonionic surfactant class useful with the present invention are the alkylene oxide-treated alkyl phenols such as the ethylene oxide alkyl phenol condensates sold by the Rohm & Haas Company. A specific example of these is Triton X-100 which contains an average of 9-10 ethylene oxide units per molecule, has an HLB value of about 13.5 and a molecular weight of about 628. Many other suitable nonionic surfactants are known; see, for example, the aforementioned McCutcheon's as well as the treatise "Non-ionic Surfactants" edited by Martin J. Schick, M. Dekker Co., New York, 1967, which is hereby incorporated by reference for its disclosures in this regard.

As noted above, cationic, anionic and amphoteric surfactants can also be used. Generally, these are all hydrophilic surfactants. Anionic surfactants contain negatively charged polar groups while cationic surfactants contain positively charged polar groups. Amphoteric dispersants contain both types of polar groups in the same molecule. A general survey of useful surfactants is found in Kirk-Othmer Encyclopedia of Chemical Technology, Second Edition, Volume 19, page 507 et seq. (1969, John Wiley and Son, New York) and the aforementioned compilation published under the name of McCutcheon's. These references are both hereby incorporated by reference for their disclosures relating to cationic, amphoteric and anionic surfactants.

Among the useful anionic surfactant types are the widely known carboxylate soaps, organo sulfates, sulfonates, sulfocarboxylic acids and their salts, and phosphates. Useful cationic surfactants include nitrogen compounds such as amine oxides and the well-known quaternary ammonium salts. Amphoteric surfactants include amino acid-type materials and similar types. Various cationic, anionic and amphoteric dispersants are available from the industry, particularly from such companies as Rohm & Haas and Union Carbide Corporation, both of America. Further information about anionic and cationic surfactants also can be found in the texts "Anionic Surfactants", Parts II and III, edited by W. M. Linfield, published by Marcel Dekker, Inc., New York, 1976 and "Cationic Surfactants", edited by E. Jungermann, Marcel Dekker, Inc., New York, 1976. Both of these references are incorporated by reference for their disclosures in this regard.

These surfactants, when used, are generally employed in effective amounts to reduce the viscosity of aqueous systems of the invention and/or aid in the dispersal of the various other additives, particularly the functional additives discussed below, in such systems.

The functional additives are typically oil-soluble, water-insoluble additives which function in conventional oil-based systems as E.P. (extreme pressure) agents, anti-wear agents, load-carrying agents, friction modifiers, and lubricity agents. They can also function as anti-slip agents, film formers, friction modifiers and lubricity agents in other compositions. As is well known, such additives can function in two or more of the above-mentioned ways; for example, E.P. agents often function as load-carrying agents also.

The term "oil-soluble, water-insoluble functional additive" refers to a functional additive which is not soluble in water above a level of about 1 gram per 100 milliliters of water at 25°, but is soluble in mineral oil to the extent of at least one gram per liter at 25°.

The functional additives of this invention also include certain solid lubricants such as graphite, molybdenum disulfide and polytetrafluoroethylene and related solid polymers.

The functional additive can also include frictional polymer formers. Briefly, these are potential polymer forming materials which are dispersed in a liquid carrier at low concentration and which polymerize at rubbing or contacting surfaces to form protective polymeric films on the surfaces. The polymerizations are believed to result from the heat generated by the rubbing and, possibly, from catalytic and/or chemical action of the freshly exposed surface. A specific example of such materials is dilinoleic acid and ethylene glycol combinations which can form a polyester frictional polymer film. These materials are known to the art and descriptions of them are found, for example, in the journal "Wear", Volume 26, pages 369-392, and West German Published Patent Application No. 2,339,065. These disclosures are hereby incorporated by reference for their discussions of frictional polymer formers.

Typically the functional additive is a known metal or amine salt of an organo sulfur, phosphorus, boron or carboxylic acid which is the same as or of the same type as used in oil-based fluids. Typical such salts are of (1) carboxylic acids of 1 to 22 carbon atoms including both aromatic and aliphatic acids; (2) sulfur acids such as alkyl and aromatic sulfonic acids and the like; phosphorus acids such as phosphoric acid, phosphorus acid, phosphinic acid, acid phosphate esters and analogous sulfur homologs such as the thiophosphoric and dithiophosphoric acid and related acid esters; boron acids include boric acid, acid borates and the like. Useful functional additives also include metal dithiocarbamates such as molybdenum and antimony dithiocarbamates; as well as dibutyl tin sulfide, tributyl tin oxide, phosphates and phosphites; borate amine salts, chlorinated waxes; trialkyl tin oxide, molybdenum phosphates, and chlorinated waxes.

Mainly such functional additives are known to the art. For example, descriptions of additives useful in conventional oil-based systems and in the aqueous systems of this invention are found in "Advances in Petroleum Chemistry and Refining," Volume 8, Edited by John J. McKetta, Interscience Publishers, New York, 1963, pages 31-38 inclusive; Kirk-Othmer "Encyclopedia of Chemical Technology," Volume 12, Second Edition, Interscience Publishers, New York, 1967, page 575 et seq.; "Lubricant Additives" by M. W. Ranney, Noyes Data Corporation, Park Ridge, N.J., U.S.A., 1973; and "Lubricant Additives" by C. V. Smalheer and R. K. Smith, The Lezius-Hiles Co., Cleveland, Ohio, U.S.A. These are hereby incorporated by reference for their disclosures of functional additives useful in the compositions or systems of this invention.

In certain of the typical aqueous systems of the invention, the functional additive is a sulfur or chloro-sulfur extreme pressure agent, known to be useful in oil-base systems. Such materials include chlorinated aliphatic hydrocarbons, such as chlorinated wax; organic sulfides and polysulfides, such as benzyldisulfide, bis-(chlorobenzyl)disulfide, dibutyl tetrasulfide, sulfurized sperm oil, sulfurized methyl ester of oleic acid, sulfurized alkylphenol, sulfurized dipentene, sulfurized terpene, and sulfurized Diels-Alder adducts; phosphosulfurized hydrocarbons, such as the reaction product of phosphorus sulfide with turpentine or methyl oleate; phosphorus esters such as the dihydrocarbon and trihydrocarbon phosphites, i.e., dibutyl phosphite, diheptyl phosphite, dicyclohexyl phosphite, pentylphenyl phosphite, dipentylphenyl phosphite, tridecyl phosphite, distearyl phosphite and polypropylene substituted phenol phosphite; metal thiocarbamates, such as zinc dioctyldithiocarbamate and barium heptylphenol dithiocarbamate; and Group II metal salts of phosphorodithioic acid, such as zinc dicyclohexyl phosphorodithioate, and the zinc salts of a phosphorodithioic acid.

The functional additive can also be a film former such as a synthetic or natural latex or emulsion thereof in water. Such latexes include natural rubber latexes and polystyrene butadienes synthetic latex.

The functional additives can also be anti-chatter or anti-squawk agents. Examples of the former are the amide metal dithiophosphate combinations such as disclosed in West German Patent No. 1,109,302; amine salt-azomethine combinations such as disclosed in British patent specification No. 893,977; or amine dithiophosphate such as disclosed in U.S. Pat. No. 3,002,014. Examples of anti-squawk agents are N-acylsarcosines and derivatives thereof such as disclosed in U.S. Pat. Nos. 3,156,652 and 3,156,653; sulfurized fatty acids and esters thereof such as disclosed in U.S. Pat. Nos. 2,913,415 and 2,982,734; and esters of dimerized fatty acids such as disclosed in U.S. Pat. No. 3,039,967. The above-cited patents are incorporated hereby by reference for their disclosure as pertinent to anti-chatter and anti-squawk agents useful as a functional additive in the aqueous systems of the present invention.

Specific examples of functional additives useful in the aqueous systems of this invention include the following commercially available products.

TABLE I

| Functional Additive Tradename | Chemical Description | Supplier |
|---|---|---|
| Anglamol 32 | Chlorosulfurized hydrocarbon | Lubrizol[1] |
| Anglamol 75 | Zinc dialkyl phosphate | Lubrizol[1] |
| Molyvan L | A thiaphosphomolybdate | Vanderbilt[2] |
| Lubrizol-5315 | Sulfurized cyclic carboxylate ester | Lubrizol[1] |
| Emcol TS 230 | Acid phosphate ester | Witco[3] |

[1]The Lubrizol Corporation, Wickliffe, Ohio, U.S.A.
[2]R. T. Vanderbilt Company, Inc., New York, N.Y., U.S.A.
[3]Witco Chemical Corp., Organics Division, Houston, Texas, U.S.A.

Mixtures of two or more of any of the aforedescribed functional additives can also be used.

Typically, a functionally effective amount of the functional additive is present in the aqueous systems of this invention. For example, if the functional additive is intended to serve primarily as a load-carrying agent, it is present in a load-carrying amount.

The aqueous systems of this invention often contain at least one inhibitor for corrosion of metals. These inhibitors can prevent corrosion of either ferrous or non-ferrous metals (e.g., copper, bronze, brass, titanium, aluminum and the like) or both. The inhibitor can be organic or inorganic in nature. Usually it is sufficiently soluble in water to provide a satisfactory inhibiting action though it can function as a corrosion inhibitor without dissolving in water, it need not be water-soluble. Many suitable inorganic inhibitors useful in the aqueous systems of the present invention are known to those skilled in the art. Included are those described in "Protective Coatings for Metals" by Burns and Bradley, Reinhold Publishing Corporation, Second Edition, Chapter 13, pages 596-605. This disclosure relative to inhibitors are hereby incorporated by reference. Specific examples of useful inorganic inhibitors include alkali metal nitrites, sodium di- and tri-polyphosphate, potassium and dipotassium phosphate, alkali metal borate and mixtures of the same. Many suitable organic inhibitors are known to those of skill in the art. Specific examples include hydrocarbyl amine and hydroxy-substituted hydrocarbyl amine neutralized acid compound, such as neutralized phosphates and hydrocarbyl phosphate esters, neutralized fatty acids (e.g., those having about 8 to about 22 carbon atoms), neutralized aromatic carboxylic acids (e.g., 4-tertiarybutyl benzoic acid), neutralized naphthenic acids and neutralized hydrocarbyl sulfonates. Mixed salt esters of alkylated succinimides are also useful. Particularly useful amines include the alkanol amines such as ethanol amine, diethanol amine, triethanol amine and the corresponding propanol amines. Mixtures of two or more of any of the afore-described corrosion inhibitors can also be used. The corrosion inhibitor is usually present in concentrations in which they are effective in inhibiting corrosion of metals with which the aqueous composition comes in contact.

The aqueous systems of the present invention can also include at least one shear stabilizing agent. Such shear stabilizing agents are especially useful where the system is intended to function as a hydraulic fluid. The shear stabilizing agent functions to make the viscosity of the aqueous system substantially independent of the shear applied to the fluid. Representative examples of such shear stabilizing agents include polyoxyalkylene polyols, particularly those where the alkylene group is an ethylene group, propylene group, or mixture of such groups and tetrasodium pyrophosphate. A specific shear stabilizing agent is available under the tradename Pluracol V-10 from BASF-Wyandotte Corporation, Wyandotte, Mich., U.S.A., Pluracol V-10 is a polyoxypropylene polyol having a viscosity at 38° C. of about 45,000 cSt. Typically, the shear stabilizing agent, when present, is present in a shear stabilizing amount.

Certain of the aqueous systems of the present invention (particularly those that are used in cutting or shaping of metal) can also contain at least one polyol with inverse solubility in water. Such polyols are those that become less soluble as the temperature of the water increases. They thus can function as surface lubricity agents during cutting or working operations since, as the liquid is heated as a result of friction between a metal workpiece and worktool, the polyol of inverse solubility "plates out" on the surface of the workpiece, thus improving its lubricity characteristics.

The aqueous systems of the present invention can also include at least one bacteriocide. Such bacteriocides are well known to those of skill in the art and specific examples can be found in the aforementioned McCutcheon publication "Functional Materials" under the heading "Antimicrobials" on pages 9-20 thereof. This disclosure is hereby incorporated by reference as it relates to suitable bacteriocides for use in the aqueous compositions or systems of this invention. Generally, these bacteriocides are water-soluble, at least to the extent to allow them to function as bacteriocides.

The aqueous systems of the present invention can also include such other materials as dyes, e.g., an acid green dye; water softeners, e.g., ethylene diamine tetraacetate sodium salt or nitrilo triacetic acid; odor masking agents, e.g., citronella, oil of lemon, and the like; and anti-foamants, such as the well-known silicone anti-foamant agents.

The aqueous systems of this invention may also include an anti-freeze additive where it is desired to use the composition at a low temperature. Materials such as ethylene glycol and analogous polyoxyalkylene glycols can be used as anti-freeze agents. Clearly, the amount used will depend on the degree of anti-freeze protection desired and will be known to those of ordinary skill in the art.

It should also be noted that many of the ingredients described above for use in making the aqueous systems of this invention are industrial products which exhibit or confer more than one property on the composition. Thus, a single ingredient can provide several functions thereby eliminating or reducing the need for some other additional ingredient. Thus, for example, an E.P. agent such as tributyl tin oxide can also function as a bactericide.

Illustrative aqueous concentrates within the scope of this invention are identified in Table II. Illustrative water-based functional fluids within the scope of this invention are identified in Table III. The numerical values indicated in these tables are in parts by weight.

TABLE II

|  | A | B |
| --- | --- | --- |
| Polyisobutenyl (950 mol. wt.) substituted succinic anhydride/-ethanolamine/diethylethanolamine reaction product | 22 | 22 |
| Product of Example 1 | 10.3 | 5.1 |
| Triton X-100 | 6.9 | 6.9 |
| Zn Salt of O,O—di(isooctyl) phosphorodithioic acid | — | 5.2 |
| Dimethylethanol Amine | 2.0 | 2.0 |
| Water | 58.8 | 58.8 |

TABLE III

|  | A | B | C | D |
| --- | --- | --- | --- | --- |
| Product of Example 1 | — | 5.2 | 5.2 | 5.2 |
| Product of Example 2 | 5.2 | — | — | — |
| Product of Example 3 | 1.8 | 1.8 | 1.8 | 1.8 |
| Polyisobutenyl (950 mol. wt.) substituted succinic anhydride/ethanolamine/-diethylethanolamine reaction product | 1.25 | 1.25 | 1.25 | 1.25 |
| Triton X-100 | 0.345 | 0.345 | 0.345 | 0.345 |
| Zinc salt of O,O—di-(isoctyl) phosphorodithioic acid | 0.51 | 0.51 | 0.51 | 0.51 |
| Dimethylethanolamine | 0.065 | 0.065 | 0.065 | 0.065 |
| Nacap, product of Vanderbilt Chemical identified as 50% aqueous solution of sodium salt of mercaptobenzothiazole | 0.5 | 0.5 | 1.0 | 1.0 |
| Sodium benzoate | — | — | 0.1 | — |
| Water | 90.3 | 90.3 | 89.7 | 89.8 |

While the invention has been explained in relation to its preferred embodiments, it is to be understood that various modifications thereof will become apparent to those skilled in the art upon reading the specification. Therefore, it is to be understood that the invention disclosed herein is intended to cover such modifications as fall within the scope of the appended claims.

I claim:
1. A composition comprising an aqueous phase and dispersed or dissolved in said aqueous phase an organo-borate compound having the formula

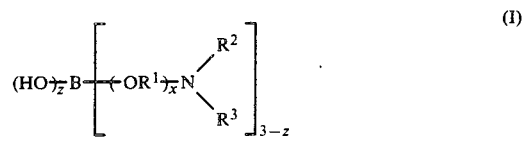

or

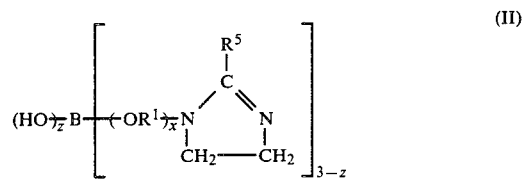

wherein
$R^1$ is a divalent hydrocarbon-based group,
$R^2$ is a hydrocarbon-based group or a group of the formula $-(R^4O)_yH$,
$R^3$ and $R^5$ are hydrocarbon-based groups,
$R^4$ is a divalent hydrocarbon-based group,
x is a integer of at least 1,
y is an integer of at least 1,
the sum of x and y has an average in the range of about 2 to about 75, and
z is 0, 1 or 2,
said composition containing a sufficient amount of water to disperse or dissolve the organo-borate compound.

2. The composition of claim 1 wherein said aqueous phase is the continuous phase of said composition.

3. The composition of claim 1 wherein said organo-borate compound has Formula (I).

4. The composition of claim 1 wherein said organo-borate compound has Formula (II).

5. The composition of claim 1 wherein $R^1$ has an average of from 1 to about 8 carbon atoms.

6. The composition of claim 1 wherein $R^1$ is ethylene or propylene.

7. The composition of claim 3 wherein $R^2$ is a hydrocarbon-based group having an average of 1 to about 100 carbon atoms.

8. The composition of claim 3 wherein $R^2$ has the structure $-(R^4O)_yH$ and $R^4$ has an average of from 1 to about 8 carbon atoms.

9. The composition of claim 8 wherein $R^4$ is ethylene or propylene.

10. The composition of claim 3 wherein the sum of x and y has an average in the range of about 2 to about 15.

11. The composition of claim 3 wherein $R^3$ has an average of 1 to about 100 carbon atoms.

12. The composition of claim 3 wherein $R^3$ has an average of about 8 to about 25 carbon atoms.

13. The composition of claim 4 wherein $R^5$ has an average of 1 to about 100 carbon atoms.

14. The composition of claim 4 wherein $R^5$ has an average of about 8 to about 25 carbon atoms.

15. The composition of claim 1 wherein z is 0.

16. A composition comprising an aqueous phase and dispersed or dissolved in said aqueous phase an organo-borate compound of the formula

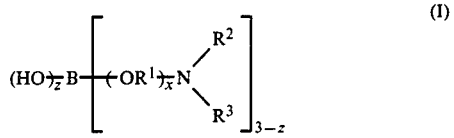

wherein $R^1$ is a lower divalent hydrocarbon-based group having an average of 1 to about 8 carbon atoms,
$R^2$ is a hydrocarbon-based group or a group having the formula $-(R^4O)_yH$ wherein $R^4$ is a lower divalent hydrocarbon-based group,
$R^3$ is a hydrocarbon-based group,
x is an integer of at least 1,
y is an integer of at least 1,
the sum of x and y has an average in the range of about 2 to about 75, and
z is 0, 1 or 2,
said composition containing a sufficient amount of water
to disperse or dissolve the organo-borate compound.

17. The composition of claim 16 wherein said aqueous phase is the continuous phase of said composition.

18. The composition of claim 16 wherein the sum of x and y has an average in the range of about 2 to about 15.

19. The composition of claim 16 wherein $R^2$ is $-(R^4O)_yH$ and $R^4$ has an average of 1 to about 8 carbon atoms.

20. The composition of claim 19 wherein $R^4$ is ethylene or propylene.

21. The composition of claim 16 wherein $R^1$ is ethylene or propylene.

22. The composition of claim 16 wherein $R^3$ has an average of 1 to about 100 carbon atoms.

23. The composition of claim 16 wherein $R^3$ has an average of about 8 to about 25 carbon atoms.

24. The composition of claim 16 wherein $R^3$ has an average of about 10 to about 20 carbon atoms.

25. The composition of claim 16 wherein $R^2$ is $-(R^4O)_yH$, and $R^1$ and $R^4$ are each ethylene.

26. The composition of claim 16 wherein $R^2$ is $-(R^4O)_yH$, $R^1$ and $R^4$ are each ethylene, $R^3$ is an alkyl group having an average of about 12 to about 18 carbon atoms, and the group

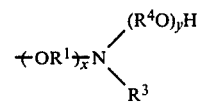

is derived from a mixture of ethoxylated fatty amines.

27. The composition of claim 16 wherein z is 0.

28. An aqueous concentrate comprising the composition of any one of claims 1–27, said concentrate comprising about 25% to about 70% by weight water.

29. A water-based functional fluid made by diluting the concentrate of claim 28 with water wherein the ratio of water to concentrate is in the range of about 80:20 to about 99:1.

30. A water-based functional fluid comprising the composition of any one of claims 1–27, said water being present in a major amount, said organo-borate compound being present in a minor thickening amount.

* * * * *